United States Patent [19]

Donofrio

[11] Patent Number: 5,283,264
[45] Date of Patent: Feb. 1, 1994

[54] CHEMICALLY STABLE ANTIMICROBIAL FORMULATIONS OF DIMPS

[75] Inventor: Deborah K. Donofrio, The Woodlands, Tex.

[73] Assignee: Betz Laboratories, Inc., Trevose, Pa.

[21] Appl. No.: 982,802

[22] Filed: Nov. 30, 1992

[51] Int. Cl.$^5$ .................. A01N 25/22; A01N 41/10
[52] U.S. Cl. ......................................... 514/709; 568/23
[58] Field of Search ................ 514/709; 504/116, 150; 568/23

[56] References Cited

U.S. PATENT DOCUMENTS 5,093,369  3/1992  Donofrio et al. .................. 514/640
5,118,713  6/1992  Donofrio et al. .................. 514/709

Primary Examiner—Allen J. Robinson
Assistant Examiner—B. Bembenick
Attorney, Agent, or Firm—Alexander D. Ricci; Richard A. Paikoff

[57] ABSTRACT

An antimicrobial composition and method for producing a stable, antimicrobial formulation of diiodomethyl-p-tolylsulfone is disclosed.

12 Claims, No Drawings

CHEMICALLY STABLE ANTIMICROBIAL FORMULATIONS OF DIMPS

FIELD OF THE INVENTION

The present invention relates to an antimicrobial composition comprising a stable mixture of diiodomethyl-p-tolylsulfone (DIMPS), a pyrrolidone compound and water.

BACKGROUND OF THE INVENTION

The formation of slimes by microorganisms is a problem that is encountered in many aqueous systems. For example, the problem is not only found in natural waters such as lagoons, lakes, ponds, etc., and confined waters as in pools, but also in such industrial systems as cooling water systems, air washer systems and pulp and paper mill systems. All possess conditions which are conducive to the growth and reproduction of slime-forming microorganisms. In both once-through and recirculating cooling systems, for example, which employ large quantities of water as a cooling medium, the formation of slime by micro-organisms is an extensive and constant problem.

Airborne organisms are readily entrained in the water from cooling towers and find this warm medium an ideal environment for growth and multiplication. Aerobic and heliotropic organisms flourish on the tower proper while other organisms colonize and grow in such areas as the tower sump and the piping and passages of the cooling system. The slime formation not only aids in the deterioration of the tower structure in the case of wooden towers, but also promotes corrosion when it deposits on metal surfaces. Slime carried through the cooling system plugs and fouls lines, valves, strainers, etc., and deposits on heat exchange surfaces. In the latter case, the impedance of heat transfer can greatly reduce the efficiency of the cooling system.

In pulp and paper mill systems, slime formed by microorganisms is commonly encountered and causes fouling, plugging, or corrosion of the system. The slime also becomes entrained in the paper produced to cause breakouts on the paper machines, which results in work stoppages and the loss of production time. The slime is also responsible for unsightly blemishes in the final product, which result in rejects and wasted output.

The previously discussed problems have resulted in the extensive utilization of biocides in cooling water and pulp and paper mill systems. Materials which have enjoyed widespread use in such applications include chlorine, chlorinated phenols, organo-bromines, and various organo-sulfur compounds. All of these compounds are generally useful for this purpose but each is attended by a variety of impediments. For example, chlorination is limited both by its specific toxicity for slime-forming organisms at economic levels and by the tendency of chlorine to react, which results in the expenditure of the chlorine before its full biocidal function is achieved. Other biocides are attended by odor problems, and hazards with respect to storage, use or handling which limit their utility. To date, no one compound or type of compound has achieved a clearly established predominance with respect to the applications discussed. Likewise, lagoons, ponds, lakes, and even pools, either used for pleasure purposes or used for industrial purposes for the disposal and storage of industrial wastes, become, during the warm weather, besieged by slime due to microorganism growth and reproduction. In the case of industrial storage or disposal of industrial materials, the microorganisms cause additional problems which must be eliminated prior to the materials use or disposal of the waste.

Naturally, economy is a major consideration with respect to all of these biocides. Such economic considerations attach to both the cost of the biocide and the expense of its application. The cost performance index of any biocide is derived from the basic cost of the material, its effectiveness per unit of weight, the duration of its biocidal or biostatic effect in the system treated, and the ease and frequency of its addition to the system treated. To date, none of the commercially available biocides has exhibited a prolonged biocidal effect. Instead, their effectiveness is rapidly reduced as a result of exposure to physical conditions such as temperature, association with ingredients contained by the system toward which they exhibit an affinity or substantivity, etc., with a resultant restriction or elimination of their biocidal effectiveness, or by dilution.

As a consequence, the use of such biocides involves their continuous or frequent addition to systems to be treated and their addition to multiple points or zones in the systems to be treated. Accordingly, the cost of the biocide and the labor cost of applying it are considerable. In other instances, the difficulty of access to the zone in which slime formation is experienced precludes the effective use of a biocide. For example, if in a particular system there is no access to an area at which slime formation occurs the biocide can only be applied at a point which is upstream in the flow system. However, the physical or chemical conditions, e.g., chemical reactivity, thermal degradation, etc., which exist between the point at which the biocide may be added to the system and the point at which its biocidal effect is desired render the effective use of a biocide impossible.

Similarly, in a system experiencing relatively slow flow, such as a paper mill, if a biocide is added at the beginning of the system, its biocidal effect may be completely dissipated before it has reached all of the points at which this effect is desired or required. As a consequence, the biocide must be added at multiple points, and even then a diminishing biocidal effect will be experienced between one point of addition to the system and the next point downstream at which the biocides may be added. In addition to the increased cost of utilizing and maintaining multiple feed points, gross ineconomies with respect to the cost of the biocide are experienced. Specifically, at each point of addition, an excess of the biocide is added to the system in order to compensate for that portion of the biocide which will be expended in reacting with other constituents present in the system or experience physical changes which impair its biocidal activity.

The toxicity of the solvents and inerts in biocide formulations is also becoming a serious concern among formulators and end-users. These human and environmental toxicity issues have made solvents such as dimethylformamide (DMF), dimethylsulfoxide (DMSO) and heavy aromatic naptha unacceptable choices for solvents in biocide products. Thus, solvents with lower toxicity and favorable environmental impact data would be more desirable alternatives.

DETAILED DESCRIPTION OF THE INVENTION

Surprisingly, it has been found that chemically stable antimicrobial compositions may be formed comprising diiodomethyl-p-tolylsulfone (DIMPS), a pyrrolidone compound, e.g., N-methyl pyrrolidone (NMP) and water.

The present invention makes possible viable antimicrobial formulations of DIMPS in a carrier which does not contain aliphatic or aromatic solvents. It also eliminates use of the dispersion/suspension, which separates with time, thus making it an unstable formulation. The water-based suspension has an additional problem in that it contains particles of the water-insoluble active. This means that the DIMPS is less bioavailable than when it has been dissolved in pyrrolidone, since this formulation more closely resembles a true solution. Thus, the pyrrolidone formulation eliminates settling, pumping and dissolution difficulties and increases the bioavailability of DIMPS in water-based industrial systems.

N-methyl pyrrolidone (NMP) was chosen for testing because it has an acceptable flash point, as well as the fact that it carries appropriate FDA/EPA approvals. NMP is commercially available. The NMP-based formulations are true solutions which are physically stable to freeze/thaw cycling.

The antimicrobial efficacy of the NMP-containing formulations is at least comparable to the efficacy of DIMPS on a 100% active basis. The DIMPS product is a water-based dispersion and is less desirable compared to a true solution product due to the standard problems associated with dispersions, e.g., the limited physical stability of the product resulting in frequent mixing of the product in the drum being needed after delivery to a plant.

The solubility of DIMPS in several solvents is illustrated in Table I.

TABLE 1

Solubility of Diiodomethyl-p-tolylsulfone in Various Solvents

| Solubility, g/L at 25° C. in: | |
|---|---|
| Water | 0.0001 |
| Isopropyl Alcohol | 10.0 |
| Acetone | 350.0 |
| Mineral Spirits | 4.0 |
| Toluene | 43.0 |
| Tributyl Phosphate | 220.0 |
| Ethanol | 20.0 |
| Ethylene Glycol | 10.0 |
| Hexane | 2.0 |
| Xylene | 33.0 |
| Dimethyl Formamide | 1,000.0 |
| n-Propyl Acetate | 263.0 |

None of the preceding solvents is acceptable for one or more of the following reasons:

1) Not an approved solvent by the EPA and/or FDA.
2) Too hazardous to use with respect to human contact on a regular basis (dimethyl formamide).
3) Solvent flash points are too low, making products based on these unsafe.

When DIMPS was mixed with NMP as the sole solvent, the resulting solution appeared to be physically stable. However, chemical stability testing at both 500° C. for 30 days and 30 days at ambient temperature in the light showed this formulation to be unstable. Solutions which had a fraction of NMP replaced with water were chemically stable under the same test conditions (see Tables 2 and 3). This was unexpected because DIMPS is extremely water insoluble. Other formulations were prepared containing particular surfactants. Surfactants which may be used include alkylphenoxy polyethoxylates, e.g., Surfonic ® (trademark of Texaco Chemical Company) N-95 or Igepal ® (trademark of GAF Corp.) RC 630, polyalkylene glycol ethers, ethoxylated fatty acids, ethylene oxide/propylene oxide block copolymers and polyethylene sorbitan fatty acid esters. It is anticipated that cationic and anionic surfactants, as well as other non-ionic surfactants would be effective.

TABLE 2

Composition of Diiodomethyl-p-tolylsulfone (DIMPS) Formulations

| Formulation | Surfactant | % DIMPS | % NMP | % Water | % Surfactant |
|---|---|---|---|---|---|
| A | | 10 | 90 | 0 | 0 |
| B | | 10 | 75 | 15 | 0 |
| C | Surfonic | 10 | 50 | 14.1 | 25 |
| D | Surfonic | 10 | 50 | 20 | 19.1 |
| E | Igepal | 10 | 50 | 20 | 19.1 |

The motivation for adding water to the formulation was to decrease the amount of NMP used, consequently reducing the raw material cost of the formulation. The chemical stability of various embodiments of the present invention is found in Table 3. Reaction conditions included either ambient (room) temperature or 50° C.; reactions took place in glass or high density polyethylene containers.

TABLE 3

Chemical Stability Data

| Formulation | % Amical T = 0 | Conditions | % Amical T = 30 days | % Change |
|---|---|---|---|---|
| A | 9.98 | 50° C.-dark/glass | 4.6 | −54 |
| A | 9.67 | ambient-light/glass | 8.53 | −11.8 |
| | | ambient-dark/HDPE* | 9.14 | −5 |
| | | 50° C.-dark/HDPE | 6.59 | −31.9 |
| B | 10.1 | 50° C.-dark/glass | 9.84 | −2.6 |
| | | 50° C.-dark/HDPE | 9.62 | −4.8 |
| B | 10.1 | ambient-light/glass | 9.97 | −1 |
| | | ambient-dark/HDPE | 10.1 | 0 |
| | | 50° C.-dark/HDPE | 9.67 | −4 |
| B | 9.81 | ambient-light/glass | 9.64 | −1.7 |
| | | ambient-dark/HDPE | 9.71 | −1.0 |
| | | 50° C.-dark/HDPE | 8.94 | −8.9 |
| C | 10.2 | 50° C.-dark/HDPE | 9.71 | −5 |
| D | 10.3 | 50° C.-dark/HDPE | 9.81 | −5 |
| E | 10.3 | 50° C.-dark/HDPE | 9.88 | −4 |

*HDPE - high density polyethylene

It is anticipated that an NMP and water solvent system would be effective in producing physically and/or chemically stable solutions with other biocide actives, alone or in combination, which are unstable in NMP alone. Furthermore, it is expected that any pyrrolidone compound would be effective in the present invention.

While we have shown and described herein certain embodiments of the present invention, it is intended that there be covered as well any change or modification therein which may be made without departing from the spirit and scope of the invention.

I claim:

1. A method for producing a stable, antimicrobial formulation of diiodomethyl-p-tolylsulfone, which comprises mixing the diiodomethyl-p-tolylsulfone with an amount, effective for the purpose, of each of the following components: (a) N-methyl pyrrolidone and (b) water.

2. The method as recited in claim 1 wherein a surfactant is an additional component.

3. The method as recited in claim 2 wherein the surfactant is an alkylphenoxy polyethoxylate, a polyalkylene glycol ether, an ethoxylated fatty acid, an ethylene oxide/propylene oxide block copolymer or a polyethylene sorbitan fatty acid ester.

4. The method as recited in claim 1 wherein (a) represents from about 50–75% of the formulation.

5. The method as recited in claim 1 wherein (b) represents from about 14–20% of the formulation.

6. The method as recited in claim 2 wherein the surfactant represents from about 19–25% of the formulation.

7. A chemically stable antimicrobial composition comprising a mixture of diiodomethyl-p-tolylsulfone with (a) N-methyl pyrrolidone and (b) water.

8. The composition as recited in claim 7 further comprising a sufficient amount of a surfactant.

9. The composition as recited in claim 8 wherein the surfactant is an alkylphenoxy polyethoxylate, a polyalkylene glycol ether, an ethoxylated fatty acid, an ethylene oxide/propylene oxide block copolymer or a polyethylene sorbitan fatty acid ester.

10. The composition as recited in claim 7 wherein (a) represents from about 50–75% of the mixture.

11. The composition as recited in claim 7 wherein (b) represents from about 14–20% of the mixture.

12. The composition as recited in claim 8 wherein the surfactant represents from about 19–25% of the mixture.

* * * * *